(12) United States Patent
Minoguchi et al.

(10) Patent No.: US 8,048,053 B2
(45) Date of Patent: Nov. 1, 2011

(54) TAMPON HAVING AN AUXILIARY PATCH

(75) Inventors: Ryo Minoguchi, Cincinnati, OH (US); Kelyn Anne Arora, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 456 days.

(21) Appl. No.: 12/102,588

(22) Filed: Apr. 14, 2008

(65) Prior Publication Data
US 2009/0259165 A1 Oct. 15, 2009

(51) Int. Cl.
A61F 13/15 (2006.01)
A61F 13/21 (2006.01)

(52) U.S. Cl. ............ 604/385.17; 604/385.18; 604/904; 604/11; 604/12; 604/13; 604/18

(58) Field of Classification Search ............ 604/11–18, 604/904, 385.17, 385.18
See application file for complete search history.

(56) References Cited

U.S. PATENT DOCUMENTS

| | | |
|---|---|---|
| 2,340,311 A | 2/1944 | Donovan |
| 2,440,141 A | 4/1948 | Donovan |
| 3,340,874 A | 9/1967 | Burgeni |
| 4,211,225 A | 7/1980 | Sibalis |
| 4,226,237 A | 10/1980 | Levesque |
| 4,305,391 A | 12/1981 | Jackson |
| 4,662,875 A * | 5/1987 | Hirotsu et al. ............. 604/389 |
| 5,047,024 A * | 9/1991 | Glassman ............. 604/380 |
| 5,728,081 A | 3/1998 | Baer et al. |
| 5,752,945 A | 5/1998 | Mosley et al. |
| 6,315,763 B1 | 11/2001 | Albright et al. |
| 6,506,958 B2 | 1/2003 | Williams |
| 6,743,212 B1 | 6/2004 | Cole et al. |
| 7,192,421 B2 | 3/2007 | Hasse et al. |
| 2006/0167428 A1* | 7/2006 | Denti et al. ............. 604/385.17 |
| 2008/0275411 A1 | 11/2008 | Hughes et al. |
| 2008/0275418 A1 | 11/2008 | Hughes et al. |

FOREIGN PATENT DOCUMENTS
WO    WO 00/18345    4/2000

OTHER PUBLICATIONS
PCT International Search Report dated Jul. 13, 2009.

* cited by examiner

*Primary Examiner* — Jacqueline F Stephens
(74) *Attorney, Agent, or Firm* — Andrew J. Hagerty; Amanda T. Barry (57) ABSTRACT

A tampon having an auxiliary patch. The tampon can include a compressed absorbent member having an insertion end, a withdrawal end, a longitudinal axis, and a body disposed between the insertion end and the withdrawal end. The compressed absorbent member can have an exterior surface. In addition, the tampon can include an auxiliary patch that can partially cover the exterior surface of the compressed absorbent member. The tampon can also include an overwrap.

15 Claims, 4 Drawing Sheets

Fig. 8 ately cover the exterior surface of the compressed absorbent member. In certain embodiments, the overwrap at least partially covers the auxiliary patch.

TAMPON HAVING AN AUXILIARY PATCH

FIELD OF THE INVENTION

The invention relates to tampons having an auxiliary patch, and more particularly, to tampons having a compressed absorbent member and an auxiliary patch partially covering the compressed absorbent member.

BACKGROUND OF THE INVENTION

Tampons for feminine hygiene are typically used within a woman's vagina to absorb body exudates, such as menstrual fluids. Tampons are generally categorized by absorbency level to enable women to select a tampon that provides optimal leakage protection, that is, the tampon should prevent menstrual discharges from leaking out of the user's body. Absorbency level is generally regulated and publicized, such as, e.g., on the tampon package, wrapper, and/or applicator of the tampon, to assist women in selecting the proper tampon. Women often experience unexpected leakage, however, even though they believe they have chosen a tampon with the correct absorbency level. This unexpected leakage can contribute to a feeling of anxiety in the consumer during use.

Because tampons are typically used within a woman's vagina, a user generally cannot evaluate how the tampon is performing during use by viewing the tampon. Instead, a user may evaluate the effectiveness of the tampon based on whether or not the user experiences leakage. A user may also evaluate effectiveness of the tampon based on the appearance of the tampon after use and/or before use. For example, a user may view the tampon post-use to determine the distribution of menstrual fluid within the tampon and/or may view the tampon pre-use to visually identify any leakage protection features that may be apparent. Thus, tampon appearance can provide information to a user that can potentially alleviate feelings of anxiety with respect to unexpected leakage.

As such, it would be desirable to provide a tampon having improved leakage protection. It would also be desirable to provide a tampon having an improved visual appearance before and/or after use.

SUMMARY OF THE INVENTION

Tampons having an auxiliary patch are provided. The tampon can have an outer surface and can include a compressed absorbent member having an insertion end, a withdrawal end, a longitudinal axis, and a body disposed between the insertion end and the withdrawal end. The compressed absorbent member can have an exterior surface. In certain embodiments, the tampon can include an auxiliary patch partially covering the exterior surface of the compressed absorbent member. In addition, the tampon can include an overwrap substantially covering the exterior surface of the compressed absorbent member. In certain embodiments, the overwrap at least partially covers the auxiliary patch.

Also provided are tampons having an outer surface, the tampons including a compressed absorbent member having an insertion end, a withdrawal end, a longitudinal axis, and a body disposed between the insertion end and the withdrawal end. In certain embodiments, the compressed absorbent member can have an exterior surface that corresponds to the outer surface of the tampon, and an auxiliary patch partially covering the outer surface.

Also provided are tampons having an outer surface, a compressed absorbent member having an insertion end, a withdrawal end, a longitudinal axis, and a body disposed between the insertion end and the withdrawal end. The compressed absorbent member can have an exterior surface. In certain embodiments, the tampon can include an overwrap at least partially covering the exterior surface, the overwrap having a first surface corresponding to the outer surface of the tampon and a second surface opposite the first surface. In addition, the tampon can include an auxiliary patch partially covering the first surface of the overwrap.

DETAILED DESCRIPTION OF THE INVENTION

Tampons having a compressed absorbent member and one or more auxiliary patches are provided. In certain embodiments, the tampon can include an overwrap, such as, e.g., a fluid pervious overwrap. The auxiliary patch can be provided at any suitable location, such as, e.g., partially covering the compressed absorbent member, such as, e.g., contacting the compressed absorbent member, provided between the compressed absorbent member and the overwrap, or joined to the overwrap and/or compressed absorbent member on either the interior or exterior surface. In certain embodiments, the auxiliary patch can be provided on a carrier layer, such as, e.g., a layer disposed exterior to the compressed absorbent member, such as, e.g., on the compressed absorbent member, between the compressed absorbent member and an overwrap, or exterior to the compressed absorbent member and overwrap. In certain embodiments, the auxiliary patch can be provided prior to compression of the absorbent material into a compressed absorbent member.

Such auxiliary patches, in certain embodiments, can improve fluid acquisition and distribution into and along the tampon. For example, an auxiliary patch can enhance fluid communication between an overwrap and absorbent core of the tampon, such as, e.g., by providing a surface energy gradient and/or by being joined to one or more of the overwrap and/or absorbent core. In certain embodiments, an auxiliary patch can distribute fluid to a desired location on the tampon, such as, e.g., when the auxiliary patch is made of wicking material such as, e.g., capillary channel fibers, or when the auxiliary patch is made of impermeable material. In addition, or alternatively, an auxiliary patch can provide improved fluid acquisition and distribution that can result in faster tampon expansion and/or better vaginal coverage, which can, e.g., improve the leakage protection abilities of the tampon. Additional or alternative benefits provided by an auxiliary patch can include, for example, enhanced fluid masking in the patch area, such as, e.g., when the auxiliary patch is opaque or a suitable color for masking.

In certain embodiments, an auxiliary patch can improve the mechanics of tampon expansion, such as, e.g., when the auxiliary patch has resiliency, such as, e.g., when the patch is made of springy, resilient, or expandable fibers, foams, sponges, and/or any other suitable material, such that the auxiliary patch can enhance tampon expansion. In addition, or alternatively, the patch can provide increased tampon thickness during use, such as, e.g., to allow the tampon to better conform to the vaginal tissue, such as, e.g., when the auxiliary patch includes expandable fibers, foams, sponges, and/or any other suitable material.

An auxiliary patch can also be used to communicate information, such as, e.g., information about the tampon, to a consumer. For example, in certain embodiments, an auxiliary patch can be provided such that the auxiliary patch communicates pre-use information to a consumer, such as, e.g., actual and/or perceived absorbency regions of the tampon, tampon size, tampon shape, tampon fit, scent, comfort, or other pre-use information. In addition, or alternatively, an auxiliary patch can be provided such that the auxiliary patch communicates a post-use visual signal, such as, e.g., fluid absorbency, fluid distribution, and/or fluid masking. In certain embodiments, an auxiliary patch can communicate the perception of a fluid barrier to a consumer.

As used herein, the term "tampon" refers to any type of absorbent structure that is inserted into the vaginal canal for the absorption of fluid therefrom. Typically, tampons are constructed from an absorbent material that has been compressed into a vaginally insertable shape.

As used herein, the terms "pledget" or "tampon pledget" are intended to be interchangeable and refer to a construction of absorbent material prior to the compression of such construction into a tampon.

As used herein, the terms "vaginal cavity," "within the vagina," and "vaginal interior," are intended to be synonymous and refer to the internal genitalia of the human female in the pudendal region of the body. The term "vaginal canal," as used herein, is intended to refer to the space located between the introitus of the vagina (sometimes referred to as the sphincter of the vagina) and the cervix and is not intended to include the interlabial space, including the floor of the vestibule. The externally visible genitalia generally is not included within the term "vaginal canal" as used herein.

As used herein, "fluid pervious" refers to the property of a material and can be characterized by the ability to carry fluid or moisture, such as by capillary action, prior to any post-processing step, such as aperturing. Therefore, for example, an untreated woven or nonwoven material is fluid pervious and a thermoplastic film is not. A nonwoven material can permit fluid flow via the interstices between fibers, such as, e.g., by capillary action and/or via a pressure differential from one side of the nonwoven to the other such as the pressure experienced by a tampon in use.

As used herein, the term "fluid impervious" refers to the property of a material and can be characterized by the ability to substantially impede the passage of fluid or moisture prior to any post-processing step such as aperturing.

As used herein, "aperture" refers to a macroscopic opening or "hole" as distinct from inherent pores or interstices of fluid pervious materials, such as inherent pores or interstices of foams or nonwoven materials, for example. A macroscopic opening is visible to the naked eye of an observer having 20/20 vision at a distance of 45 cm.

As used herein, "three-dimensional aperture" refers to an aperture having a greater thickness proximate an aperture than at a non-apertured point on the overwrap under zero compression. For example, in certain embodiments, a three-dimensional aperture can include a macroscopic opening or hole having one or more protuberances or sidewalls projecting generally outwardly from the surface of the web under zero compression. In certain embodiments, a three-dimensional aperture can include one or more sidewalls substantially extending outwardly form the surface of the web around the periphery of the aperture under zero compression. A three-dimensional aperture typically has a ratio of sidewall height to material thickness greater than one, such as, e.g., greater than about 1.5, greater than about 2, greater than about 2.5, or greater than about 3.

As used herein, "vaginally insertable shape" refers to the geometrical form of the absorbent tampon after compression. The tampon can be compressed into a generally cylindrical configuration in the radial direction along the longitudinal and/or lateral axes, axially, or in both the radial and axial directions. An example of a typical compressed tampon is one which is about 10-16 mm wide and about 30-55 mm long depending on absorbency. While the tampon may be compressed into a substantially cylindrical configuration, other shapes are possible. These may include shapes having a cross section that can be described as rectangular, triangular, trapezoidal, semi-circular, hourglass, or other suitable shapes.

As used herein, a first material can "substantially cover" a second material when the first material covers at least about 75%, such as, e.g., at least about 80%, at least about 90%, at least about 95%, or about 100% of the surface area of the second material. A first material can "substantially cover" the exterior surface of a second material when the first material covers at least about 75%, such as, e.g., at least about 80%, at least about 90%, at least about 95%, or about 100% of the exterior surface of the second material.

The term "joined" or "attached," as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

The term "rolled," as used herein, refers to the configuration of the compressed absorbent member after winding the absorbent material in a spiral round and round upon itself.

The term "folded," as used herein, refers to the configuration of the compressed absorbent member that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, the term "color" includes any color, such as, e.g., white, black, red, orange, yellow, green, blue, violet, brown, and/or any other color.

As used herein, the term "image" refers to any type of mark, figure, picture, illustration, symbol, icon, pattern, or any other indicia having a purpose of providing information, such as, e.g., source information and/or a signal or guide, to the consumer.

Figure 1:
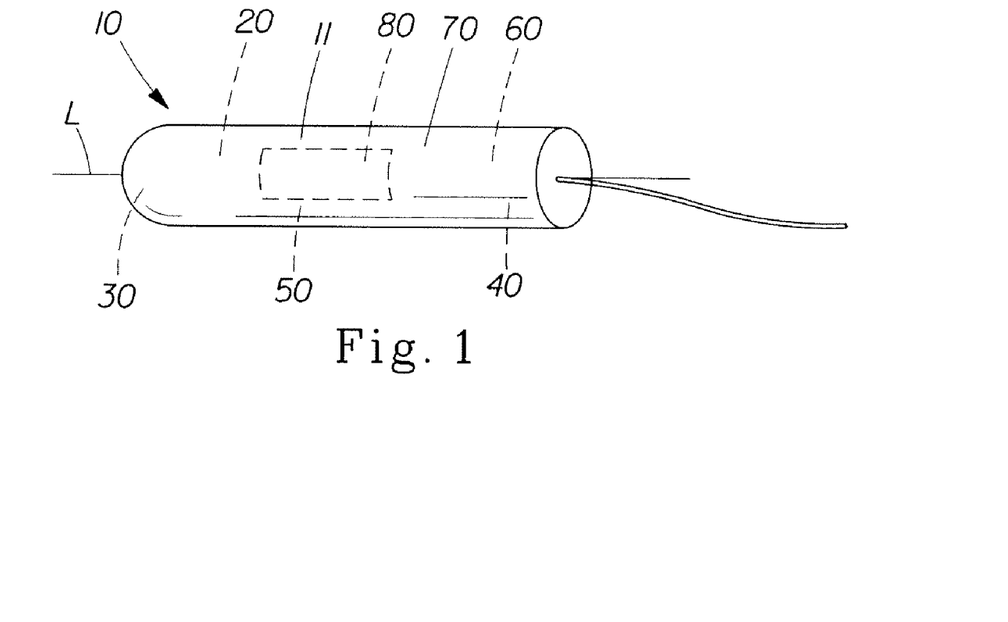
FIG. 1 is a perspective view of one embodiment of the present invention.

FIG. 1 shows an absorbent tampon 10 that has an outer surface 11. A compressed absorbent member 20 (sometimes referred to as the "absorbent core") of the tampon 10 can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. As shown in FIG. 1, the tampon 10 can have an auxiliary patch 80, such as, e.g., a rectangular shaped auxiliary patch 80.

In certain embodiments, the auxiliary patch 80 can be provided between the compressed absorbent member 20 and the overwrap 70, such as, e.g., as shown in FIG. 1. In certain embodiments, the auxiliary patch 80 only partially covers the compressed absorbent member 20. The auxiliary patch 80 can be provided between the compressed absorbent member 20 and the overwrap 70 in any suitable manner, such as, e.g., by joining the auxiliary patch 80 to the compressed absorbent member 20, such as, e.g., by joining the auxiliary patch 80 to the exterior surface 60 of the compressed absorbent member 20, and/or to the overwrap 70, by providing the auxiliary patch 80 on a carrier layer disposed between the compressed absorbent member 20 and the overwrap 70, by providing the auxiliary patch 80 during manufacture such that it can be substantially retained in position such as, e.g., by the overwrap, or by providing the auxiliary patch 80 in any other suitable manner before, during, or after manufacture. In certain embodiments, the auxiliary patch 80 can partially cover the absorbent material prior to compression, such that the auxiliary patch 80 is compressed into the compressed absorbent member 20.

Figure 2:
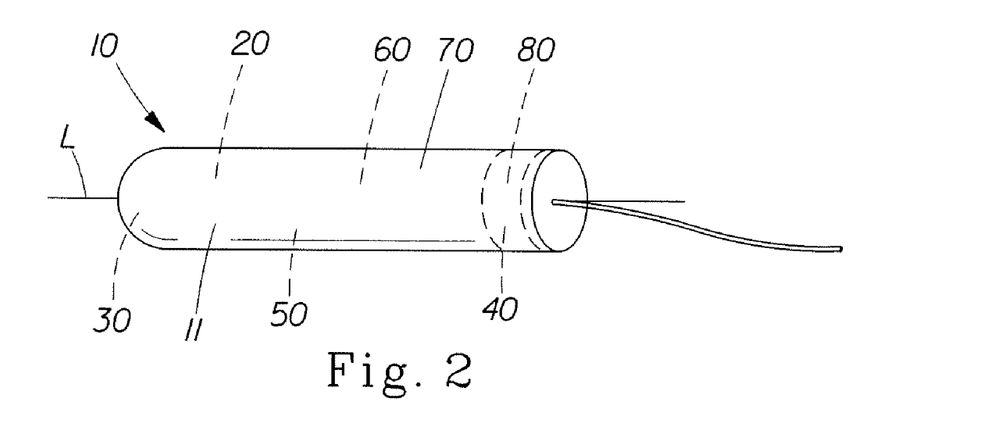
FIG. 2 is a perspective view of one embodiment of the present invention.

FIG. 2 shows an absorbent tampon 10 that has an outer surface 11. A compressed absorbent member 20 of the tampon 10 can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. As shown in FIG. 2, the tampon 10 can have an auxiliary patch 80, such as, e.g., an auxiliary patch 80 provided at the withdrawal end 40 of the tampon 10. The auxiliary patch 80 can be provided between the compressed absorbent member 20 and the overwrap 70, such as, e.g., as shown in FIG. 2. In certain embodiments, the auxiliary patch 80 can only partially cover the compressed absorbent member 20.

Figure 3:
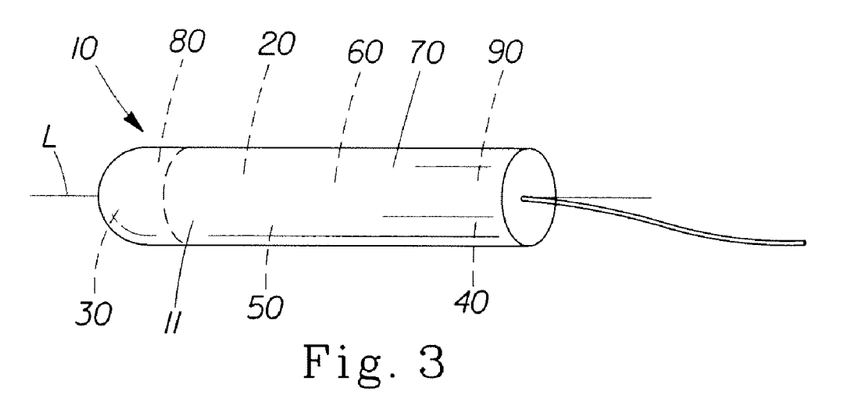
FIG. 3 is a perspective view of one embodiment of the present invention.

FIG. 3 shows an absorbent tampon 10 that has an outer surface 11. The tampon 10 can have a compressed absorbent member 20 that can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. As shown in FIG. 3, the tampon 10 can have an auxiliary patch 80, such as, e.g., an auxiliary patch 80 provided at the insertion end 30 of the tampon 10. The auxiliary patch 80 can be provided on a carrier layer 90 disposed between the compressed absorbent member 20 and the overwrap 70, such as, e.g., as shown in FIG. 3. In certain embodiments, the auxiliary patch 80 can only partially cover the compressed absorbent member 20.

Figure 4:
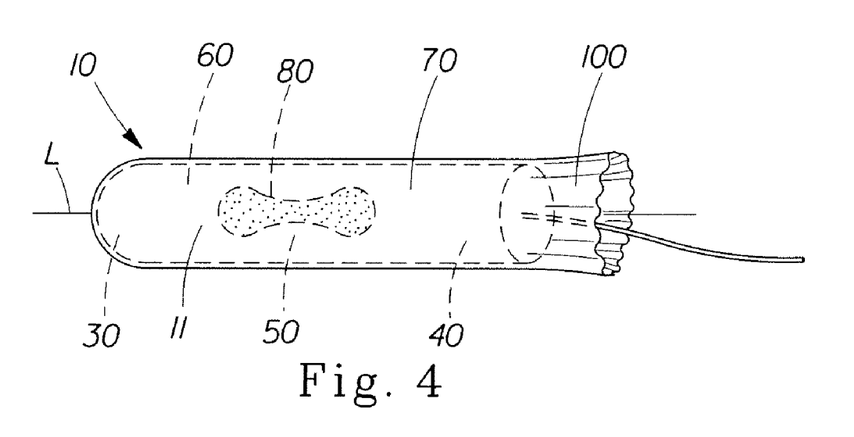
FIG. 4 is a perspective view of one embodiment of the present invention.

FIG. 4 shows an absorbent tampon 10 that has an outer surface 11. The tampon 10 can have a compressed absorbent member 20 that can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. In certain embodiments, the overwrap 70 can extend beyond the withdrawal end 40 to provide an extension 100. The extension 100 can function, for example, as a skirt portion and/or finger cover. As shown in FIG. 4, the tampon 10 can have an auxiliary patch 80, such as, e.g., an auxiliary patch 80 provided in the shape of an hourglass. In certain embodiments, as shown in FIG. 4, the auxiliary patch 80 can be one or more colors. In addition, or alternatively, the auxiliary patch 80 can be viewable by a user viewing the outer surface 11 of the absorbent tampon 10. In certain embodiments, the auxiliary patch 80 can be provided between the compressed absorbent member 20 and the overwrap 70, such as, e.g., as shown in FIG. 4. In certain embodiments, the auxiliary patch 80 can only partially cover the compressed absorbent member 20.

Figure 5:
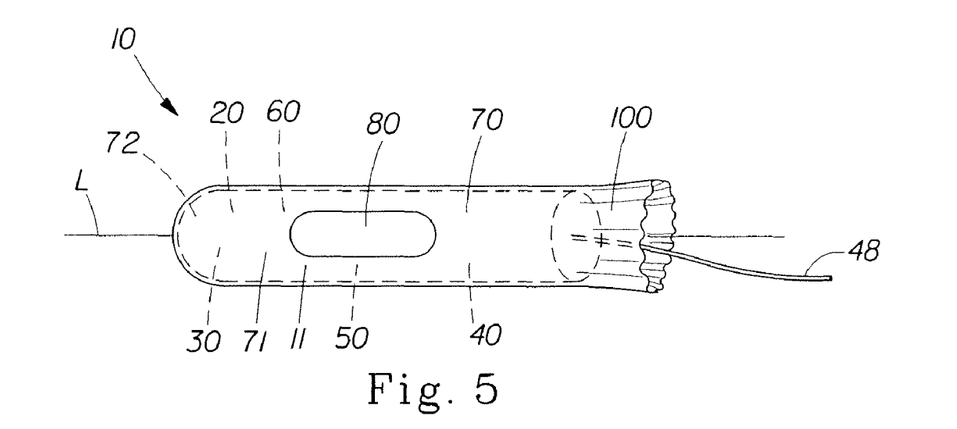
FIG. 5 is a perspective view of one embodiment of the present invention.

FIG. 5 shows an absorbent tampon 10 that has an outer surface 11. A compressed absorbent member 20 of the tampon 10 can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. The overwrap 70 can have an exterior surface 71 and an interior surface 72. In certain embodiments, the overwrap 70 can extend beyond the withdrawal end 40 to provide an extension 100. The extension 100 can function, for example, as a skirt portion and/or finger cover. As shown in FIG. 5, the tampon 10 can have an auxiliary patch 80, such as, e.g., an auxiliary patch 80 provided in the shape of an oval. The auxiliary patch 80 can partially cover the exterior surface 71 of the overwrap 70, such as, e.g., as shown in FIG. 5. In certain embodiments, the auxiliary patch 80 can be provided on the exterior surface 71 of the overwrap 70.

Figure 6:
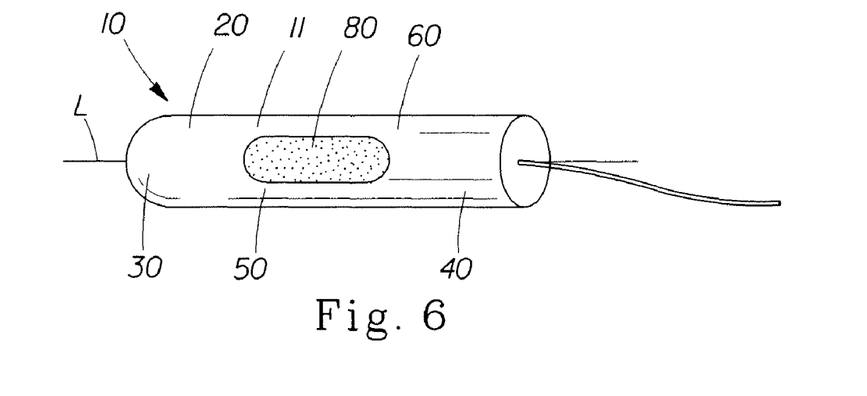
FIG. 6 is a perspective view of one embodiment of the present invention.

FIG. 6 shows an absorbent tampon 10 that has an outer surface 11. A compressed absorbent member 20 of the tampon 10 can have an insertion end 30, a withdrawal end 40, a longitudinal axis L, and a body 50 disposed between the insertion end 30 and the withdrawal end 40. The compressed absorbent member 20 can have an exterior surface 60. As shown in FIG. 6, the tampon 10 can have an auxiliary patch 80, such as, e.g., an auxiliary patch 80 provided in the shape of an oval. The auxiliary patch 80 can partially cover the exterior surface 60 of the compressed absorbent member 20, such as, e.g., as shown in FIG. 6. In certain embodiments, the auxiliary patch 80 can be one or more colors. In addition, or alternatively, the auxiliary patch 80 can be visible to a user viewing the outer surface 11.

Figure 7:
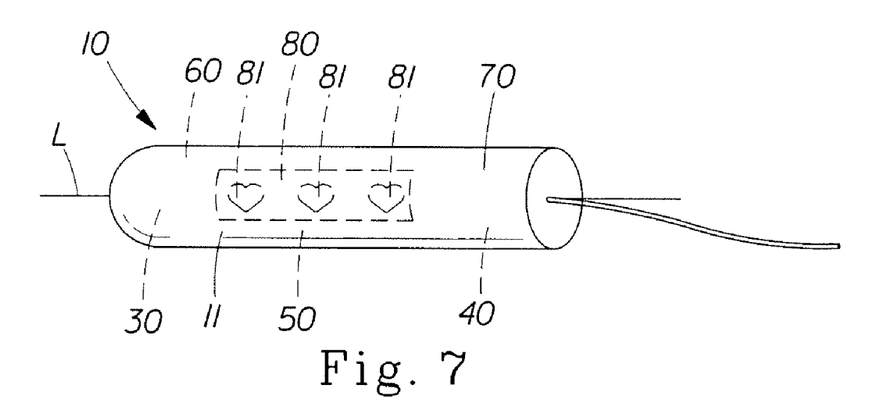
FIG. 7 is a perspective view of one embodiment of the present invention.

FIG. 7 shows an absorbent tampon 10 that has an outer surface 11. A compressed absorbent member 20 of the tampon 10 can have an insertion end 30, a withdrawal end 40, a longitudinal axis L, and a body 50 disposed between the insertion end 30 and the withdrawal end 40. The compressed absorbent member 20 can have an exterior surface 60 that can be substantially covered by an overwrap 70. As shown in FIG. 7, the tampon 10 can have an auxiliary patch 80. The auxiliary patch 80 can partially cover the compressed absorbent member 20, such as, e.g., as shown in FIG. 7. In addition, the overwrap 70 can substantially cover the auxiliary patch 80. In certain embodiments, the auxiliary patch 80 can include one or more images 81. In addition, or alternatively, the one or more images 81 can be visible to a user viewing the outer surface 11.

Figure 8:
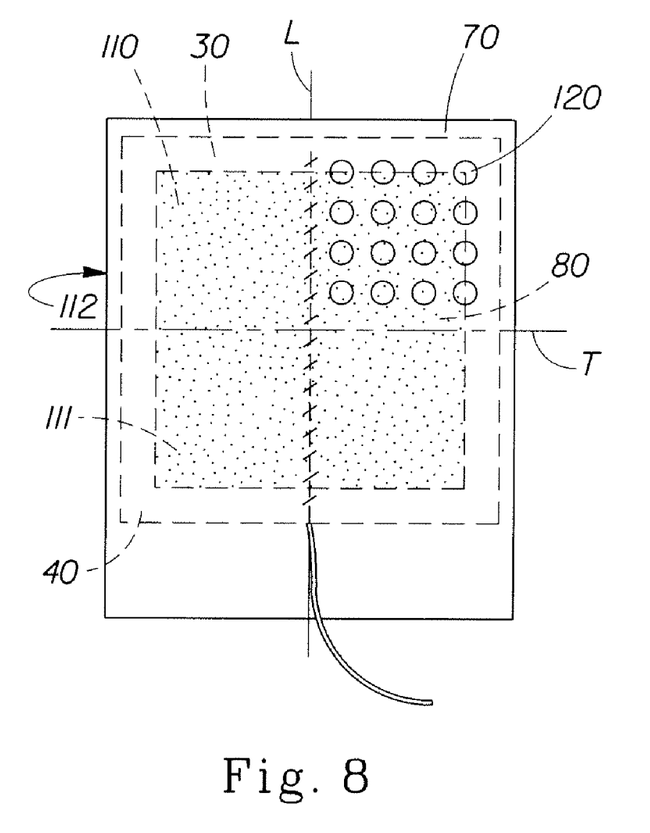
FIG. 8 is a plan view of a pledget and overwrap prior to compression.

FIG. 8 shows an absorbent pledget 110 in a flat-out configuration prior to folding and/or rolling and compression into an absorbent tampon 10. As shown in FIG. 8, the pledget 110 can be substantially covered by an overwrap 70. The absorbent pledget 110 can have a first surface 111 opposed to a second surface 112 and an insertion end 30 opposed to a withdrawal end 40. The absorbent pledget 110 can have both a longitudinal axis and a transverse axis indicated by the lines marked "L" and "T" respectively. Because the overwrap 70 can be wrapped in various configurations, the width and/or length of the overwrap 70 can be any suitable dimensions. For example, in certain embodiments, the dimensions of the overwrap 70 can be greater than, lesser than, or equal to the dimensions of the longitudinal or transverse axes of the absorbent pledget 110.

In certain embodiments, at least a portion of, such as, e.g., substantially all of, the first surface 111 of the absorbent pledget 110 can be covered by overwrap 70 prior to compression into compressed absorbent member 20. In addition, at least a portion of, such as, e.g., substantially all of, opposed second surface 112 of the absorbent pledget 110 can be covered by overwrap 70 prior to compression into compressed absorbent member 20.

In certain embodiments, the overwrap 70 can have apertures 120. In addition, the auxiliary patch 80 can be visible through the overwrap 70 by a user viewing the outer surface 11, such as, e.g., through apertures 120. In certain embodiments, the overwrap 70 can be completely apertured. Alternatively, the overwrap 70 can be partially apertured, such as, e.g., having apertures 120 generally registered to auxiliary patch 80.

The auxiliary patch can be any suitable material. Suitable materials can include, for example, materials described herein, such as, e.g., fluid pervious materials, such as, e.g., a fibrous nonwoven material comprising natural, synthetic, or a blend of natural and synthetic fibers. The fibers can be any suitable shape, such as, e.g., round, hollow, trilobal, multilobal, delta, ribbon, capillary channel/wicking, etc, or combination of shapes. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. Alternatively, or in addition, the auxiliary patch can be a fluid impervious material, such as, e.g., a plastic material, such as, e.g., one or more polymeric mesh materials. In certain embodiments, the auxiliary patch can be apertured.

The auxiliary patch can be any suitable size. In certain embodiments, the auxiliary patch can cover less than the entire exterior surface of the compressed absorbent member and/or overwrap, such as, e.g., less than about 75% of the exterior surface, less than about 50% of the exterior surface, less than about 40% of the exterior surface, less than about 30% of the exterior surface, less than about 20% of the exterior surface, or less than about 10% of the exterior surface of the compressed absorbent member and/or overwrap.

The auxiliary patch can be any suitable shape, such as, e.g., rectangle, square, circle, oval, ellipse, triangle, crescent, chevron, diamond, trapezoid, hourglass, flower, star, or any other suitable shape.

Any suitable number of auxiliary patches can be included in the tampon. For example, about one auxiliary patch, about two auxiliary patches, about three auxiliary patches, about four auxiliary patches, about five auxiliary patches, and/or any other suitable number of auxiliary patches can be included. In certain embodiments, one auxiliary patch can be provided prior to compression, wherein the auxiliary patch is viewable on two separate locations on the exterior of the compressed absorbent member after compression, such as, e.g., on a first side and on an opposite side of the compressed absorbent member. Alternatively, two auxiliary patches can be provided after compression, such as, e.g, with an auxiliary patch on a first side and an auxiliary patch on an opposite side of the compressed absorbent member.

The auxiliary patch can be provided in any suitable location. For example, in certain embodiments, the auxiliary patch can be provided on the body of the tampon, the insertion end of the tampon, and/or the withdrawal end of the tampon, or any other suitable location. In certain embodiments, one or more auxiliary patches can be located entirely on a single side of the tampon, such as, e.g., a first auxiliary patch located entirely on a first side and a second auxiliary patch located entirely on the opposite side of the first side.

The auxiliary patch can be included in the tampon in any suitable manner. In certain embodiments, the auxiliary patch can be joined to the absorbent material, such as the absorbent pledget, such as, e.g., prior to compression, joined to the compressed absorbent member, and/or joined to the overwrap. In addition, or alternatively, the auxiliary patch can be joined to a carrier layer. The auxiliary patch can be joined in any suitable manner, such as, e.g., using any suitable adhesive, heat/pressure bonding, and/or stitching, such as, e.g., with natural and/or synthetic thread.

A carrier layer can be any suitable material. In certain embodiments, the carrier layer can differ from the auxiliary patch in material, color, and/or properties, such that the auxiliary patch can be distinguished from the carrier layer.

In certain embodiments, the auxiliary patch can be visible to a user, such as, e.g., visible to a user viewing the outer surface of the tampon. The auxiliary patch can be visible by a user at any suitable time, such as, e.g., pre-use and/or post-use. In certain embodiments, the auxiliary patch can be provided on the outer surface of the tampon, such as, e.g., on the exterior surface of the overwrap or on the exterior surface of the absorbent member, such as, e.g., when the tampon does not include an overwrap, and can be visible to a user viewing the outer surface of the tampon. Alternatively, the auxiliary patch can be provided between the exterior surface of the compressed absorbent member and the overwrap and can be visible to a user viewing the outer surface of the tampon, such as, e.g., visible through the overwrap. In certain embodiments, the overwrap can be apertured and the auxiliary patch can be visible through one or more of the apertures. In addition, or alternatively, the overwrap can include apertures registered to the auxiliary patch, such as a pattern of apertures that corresponds to the size and/or shape of the auxiliary patch.

In certain embodiments, the tampon can include one or more physical patterns on the exterior surface, such as, e.g., one or more embossments, textures, channels, grooves, raised portions, and/or other suitable physical patterns. In addition, the physical pattern can be provided in registration and/or in coordination with the auxiliary patch, such as, e.g., with the shape and/or size of the auxiliary patch. In certain embodiments, the auxiliary patch can include one or more physical patterns and the tampon can include one or more physical patterns. The physical patterns can be the same, related, complementary, or different. In addition, the one or more physical patterns of the auxiliary patch and the one or more physical patterns of the tampon can be arranged such that the physical patterns are enhanced, such as, e.g., by registering the physical pattern of the auxiliary patch and the physical pattern of the tampon.

The auxiliary patch can be any suitable color. In certain embodiments, the auxiliary patch can be a color that is different from a color of the compressed absorbent member and/or overwrap, such as, e.g., a non-white color. The auxiliary patch can also be a color that contrasts with the color of the compressed absorbent member and/or overwrap, such as, e.g., such that the auxiliary patch is visible by a user viewing the tampon. In addition, or alternatively, the auxiliary patch can be a color that is the same as a color provided on the absorbent member, such as, for example, in the instance of a blue auxiliary patch and an overwrap and/or compressed absorbent member having a blue portion and a white portion, and/or a purple auxiliary patch and a purple withdrawal member. In certain embodiments, the auxiliary patch can include one or more patterns, such as, e.g., one or more printed patterns. In addition, or alternatively, the auxiliary patch can include other suitable design elements, such as, e.g., one or more textures, embossments, images, apertures, or other suitable design elements. Color and/or other design elements can be provided in any suitable manner, such as, e.g., by dying, spraying, printing, coating, pigmenting, and/or any other suitable manner. In certain embodiments, the auxiliary patch can be translucent and/or transparent.

In certain embodiments, one or more auxiliary patches can be provided to communicate information to a user. An auxiliary patch can be designed to communicate information in any suitable manner, such as, e.g., by the auxiliary patch location, auxiliary patch shape, auxiliary patch design, auxiliary patch color, and/or auxiliary patch size. Any suitable information can be provided, such as, e.g., information about the location or perceived location of a fluid barrier, a path of fluid flow, and/or a region of improved absorbency. In certain embodiments, an auxiliary patch can be provided to communicate an image, a decorative pattern, a source identifier, absorbency level, and/or a logo.

The auxiliary patch can provide one or more benefits, such as, e.g., a combination of benefits. For example, in certain embodiments, the auxiliary patch can provide a region of increased absorbency and can communicate to a consumer the location of the increased region, such as, e.g., by being a color, such as, e.g., a color different from the color of the compressed absorbent member. Alternatively, the auxiliary patch can provide a barrier and can communicate to a consumer the location of the barrier. In certain embodiments, the auxiliary patch can communicate to a consumer the location of a perceived absorbency region and can provide masking of fluid in that region. In addition, or alternatively, the auxiliary patch can increase absorption of fluid and can provide fluid masking.

The overwrap can be a fluid pervious overwrap, such as, e.g., an overwrap including a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber. The basis weight of the nonwoven overwrap prior to forming apertures can be any suitable weight, such as, e.g., from about 5 to about 60 grams per square meter (gsm), such as, e.g., from about 10 to about 30 gsm. Synthetic fibers, if used, can have hydrophobic and/or hydrophilic finishes, although, as mentioned above, in certain embodiments, the fibers of the nonwoven can be rendered hydrophobic relative to the absorbent member.

Alternatively, or in addition, the overwrap can be a fluid impervious overwrap, such as, e.g., a plastic material, such as, e.g., one or more polymeric mesh materials. In certain embodiments, the fluid impervious material can be apertured to provide for a fluid pervious overwrap.

In certain embodiments, the overwrap can be hydrophobic relative to the compressed absorbent member. Hydrophobicity can be inherent due to the material properties of the overwrap material, or the overwrap can be rendered hydrophobic by suitable treatment of an otherwise hydrophilic material. For example, the overwrap can comprise one or more fibers that are inherently more hydrophobic than the compressed absorbent member, such as, e.g., polypropylene spunbond and/or conjugate fibers, such as bicomponent polyethylene/polypropylene fibers and/or bicomponent polyethylene/polyester fibers.

Alternatively, or in addition, the overwrap can contain hydrophilic fibers, such as, e.g., rayon or a blend of rayon/cotton, that can, in certain embodiments, be rendered hydrophobic by a suitable treatment. Any suitable treatment can be employed, such as, e.g., a coating of a suitable material sufficient to render the overwrap sufficiently hydrophobic. For example, surface treatments can include applied coatings of silicone, such as Dow Corning 108® silicone, available from the Dow Corning Co. Inc., Midland, Mich.; or Sucrose Esters of Fatty Acids (SEFA), available from the Procter & Gamble Co., Inc., Cincinnati, Ohio, polyolefin waxes, or NALAN® available from DuPont, Wilmington Del. Such coatings can render the overwrap hydrophobic, or highly hydrophobic. The application of a suitable surface treatment can be achieved by spraying, slot coating, immersion and other suitable methods. The amount of coating can be varied as needed to render the overwrap sufficiently hydrophobic relative to the compressed absorbent member. In certain embodiments, a 1% by weight coating of SEFA can be utilized. Sufficient relative hydrophobicity is achieved when fluid such as menses is absorbed into the compressed absorbent member in use, and is sufficiently desorbed from the overwrap so as to partition the fluid into the core and away from the overwrap.

In certain embodiments, the overwrap can be hydrophilic relative to the compressed absorbent member. Hydrophilicity can be inherent due to the material properties of the overwrap material, or the overwrap can be rendered hydrophobic by suitable treatment. For example, the overwrap can comprise one or more fibers that are inherently more hydrophobic than the compressed absorbent member, such as, e.g., rayon and/or cotton, and/or can be rendered hydrophobic by a suitable treatment.

In certain embodiments, the overwrap can be apertured. Apertures can be of virtually any shape and size. In certain embodiments, apertures can be generally round or oblong shaped, in a regular pattern of spaced apart openings. The apertures can each have any suitable area, such as, e.g., an area of from about 0.3 mm$^2$ to about 4 mm$^2$, such as, e.g., about 2 mm$^2$, such as, e.g., about 1 mm$^2$, and can form an open area of between about 1% and about 25%, such as, e.g., between about 2% and about 20%, such as, e.g., an open area between about 10% and about 15%. In certain embodiments, the apertures can be provided in non-repeating and/or non-regular patterns that can be random and/or can have various shapes and sizes. In addition, or alternatively, the overwrap can include three-dimensional apertures.

The overwrap can be joined to the absorbent material by any variety of means. The overwrap can be joined to itself or to the absorbent material. For example, one portion of overwrap can be joined to an opposed portion of the overwrap or the absorbent member using any suitable adhesive or heat/pressure bonding means. Such adhesive can extend continuously along the length of attachment or it can be applied in a non-continuous fashion at discrete intervals. Heat bonding includes thermally bonding, fusion bonding, or any other suitable means for joining such materials. Alternatively, the overwrap may be joined to the absorbent material by stitching. Such stitching may use natural or synthetic thread.

The absorbent material can be any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911,712; 6,740,070; 6,887,266; and 6,953,456. A typical size for absorbent material prior to compression can be from about 30 mm to about 100 mm in length and from about 30 mm to about 80 mm in width. The typical range for the overall basis weight of the absorbent material 28 is from about 150 gsm to about 1250 gsm depending upon desired absorbent capacity. The materials for the tampon can be formed into a fabric, web, or batt that is suitable for use in the absorbent material by any suitable process such as airlaying, carding, wetlaying, hydroentangling, needling or other known techniques. In certain embodiments, the absorbent material can be a single pledget that can be compressed to form a tampon. The pledget can have any suitable density, such as, e.g., a substantially uniform density or varying densities.

The absorbent material can be a laminar structure comprised of integral or discrete layers. In other embodiments, the pad need not have a layered structure at all. The absorbent material may comprise a folded structure or may be rolled. The resulting compressed absorbent member of the tampon can be constructed from a wide variety of liquid-absorbing materials commonly used in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

Any suitable pressures and temperatures for compression can be used. In certain embodiments, the absorbent material and the overwrap can be compressed in the radial direction and optionally axially by any suitable means. While a variety of techniques are known and acceptable for these purposes, a tampon compressor machine available from Hauni Machines, Richmond, Va., can be suitable.

The compressed absorbent member can be formed in any suitable manner. In certain embodiments, the tampon can be a tampon having a folded construction. Alternatively, the tampon can be a tampon having a radially compressed rolled construction. The tampon can be constructed by rolling and radially compressing a pledget. The pledget can be rolled around a mandrel then compressed with or without the mandrel. In certain embodiments, a cavity left behind after the mandrel is removed can provide a finger pocket. The compressed absorbent member can also be constructed by pressing a pledget, such as, for example, a cylindrical pledget, in forming dies with a pushrod. A cavity that can be a finger pocket can be formed in part of the blank pressed against a convex in the forming dies or the pushrod. The compressed absorbent member can be any suitable dimension, such as, e.g., from about 30 mm to about 60 mm long and from about 8 to about 20 mm wide.

In certain embodiments, such as, e.g., when the tampon includes an overwrap, the absorbent material can be joined to the overwrap and can be rolled and/or folded, compressed and optionally heat conditioned in any suitable conventional manner. In certain embodiments, after rolling or folding and compression, the overwrap can cover the exterior surface of the compressed absorbent member and can also be embedded in the interior folds of the compressed absorbent member. That is, in certain embodiments, the overwrap can permeate the interior of the compressed absorbent member.

The tampon can additionally include a withdrawal member. The withdrawal member can be any suitable configuration, such as, e.g., one or more cords, strings, finger covers, ribbons, an extension of a material of the device, or combinations thereof. The withdrawal member can be made of any suitable material, such as, e.g., cotton and rayon. The withdrawal member can optionally be provided with a secondary absorbent member. Suitable secondary absorbent members are described in, e.g., U.S. Pat. No. 6,258,075.

In certain embodiments, the tampon can include a finger pocket and/or a finger indent at the withdrawal end of the tampon, such as, e.g., to aid in insertion described in, such as, e.g., U.S. Pat. No. 6,283,952. In certain embodiments, at least a portion of the withdrawal member can be at least partially disposed in the finger pocket and/or the finger indent. The finger pocket or the finger indent may be hidden in the finished tampon and appear once the user prepares the device for insertion at least partially extending the withdrawal member, and/or loosening the withdrawal end of the tampon by moving the withdrawal cord. In addition, or alternatively, the tampon can include an overwrap that extends from the withdrawal end and forms a finger cover. In certain embodiments, the tampon can include an overwrap that extends from the withdrawal end and forms an absorbent skirt. In addition, the excess of the overwrap can be at least partially disposed in a finger pocket or a finger indent and can be pulled out to provide a finger cover or an absorbent skirt when the user prepares the tampon for insertion. In certain embodiments, the excess of the overwrap can be joined with the withdrawal cord and disposed in the finger pocket or the finger indent along with the withdrawal cord, such as, for example, in U.S. patent application Ser. Nos. 11/525,553 and 11/525,730.

While several methods of making the tampon of the present invention should be apparent to one of skill in the art in light of the disclosure herein, following is a description of one method of making a tampon of the present invention.

In certain embodiments, the process for making a tampon can include the steps of providing an absorbent material having a first surface opposed to a second surface and an insertion end opposed to a withdrawal end, providing a overwrap, such as, e.g., an overwrap including one or more nonwoven materials having a material thickness, and providing one or more auxiliary patches. The overwrap can be wrapped or folded about the absorbent material to cover at least a portion of, and/or to substantially cover, one or more surfaces of the absorbent material. The wrapped absorbent can be rolled or folded and/or compressed to form a compressed absorbent member having a vaginally insertable shape. Upon compression, the overwrap can cover at least a portion and/or can substantially cover the exterior surface of the compressed absorbent member. In certain embodiments, upon compression, the auxiliary patch partially covers the exterior surface of the compressed absorbent member and also permeates into the interstices of the inner region of the compressed absorbent member.

The auxiliary patch can be provided at any suitable point during the process for making a tampon. For example, in certain embodiments, the auxiliary patch can be provided prior to the tampon forming process, such as, e.g., by adding the auxiliary patch to a component, such as, e.g., the absorbent material, the overwrap, and/or a carrier layer prior to tampon assembly. Alternatively, the auxiliary patch can be provided on the tampon converting line during the tampon forming process, such as, e.g., prior to, during, or after the formation of the tampon pledget.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial tampon having an outer surface, the tampon comprising:
   a compressed absorbent member having an insertion end, a withdrawal end, a longitudinal axis, and a body disposed between the insertion end and the withdrawal end, the compressed absorbent member having an exterior surface;
   an auxiliary patch partially covering the exterior surface of the compressed absorbent member; and
   an overwrap substantially covering the exterior surface;
   wherein the overwrap at least partially covers the auxiliary patch, and wherein the auxiliary patch comprises a carrier layer and is more hydrophilic than the overwrap to create a surface energy gradient capable of facilitating fluid movement from the overwrap to the absorbent core.

2. The tampon of claim 1, wherein the compressed absorbent member is a first color and the auxiliary patch is a second color, the first color being different from the second color.

3. The tampon of claim 1, wherein the auxiliary patch includes one or more images.

4. The tampon of claim 1, wherein the auxiliary patch is visible to a user viewing the outer surface of the tampon.

5. The tampon of claim 1, wherein the auxiliary patch is joined to the compressed absorbent member.

6. The tampon of claim 1, wherein the auxiliary patch is joined to the overwrap.

7. A catamenial tampon having an outer surface, the tampon comprising:
   a compressed absorbent member having an insertion end, a withdrawal end, a longitudinal axis, and a body disposed between the insertion end and the withdrawal end, the compressed absorbent member having an exterior surface that corresponds to the outer surface of the tampon; and
   an auxiliary patch partially covering the outer surface,
   wherein the auxiliary patch comprises channeled fibers or impermeable material to facilitate fluid distribution to a targeted area of the compressed absorbent member and
   wherein the auxiliary patch covers less than 75% of the outer surface.

8. The tampon of claim 7, wherein the compressed absorbent member is a first color and the auxiliary patch is a second color, the first color being different from the second color.

9. The tampon of claim 7, wherein the auxiliary patch includes one or more images.

10. The tampon of claim 7, further comprising an overwrap and wherein the auxiliary patch is at least partially disposed between the compressed absorbent member and the overwrap.

11. The tampon of claim 7, wherein the auxiliary patch covers less than 50% of the outer surface.

12. The tampon of claim 7, wherein the auxiliary patch covers less than 40% of the outer surface.

13. The tampon of claim 7, wherein the auxiliary patch covers less than 30% of the outer surface.

14. The tampon of claim 7, wherein the auxiliary patch covers less than 20% of the outer surface.

15. The tampon of claim 7, wherein the auxiliary patch is in the form of a nonwoven or polymeric mesh material.

* * * * *